United States Patent [19]

Fay et al.

[11] Patent Number: 4,744,667

[45] Date of Patent: May 17, 1988

[54] MICROSPECTROFLUORIMETER

[75] Inventors: Fredric S. Fay, Worcester; John F. Hatch, Framingham; Kevin E. Fogarty, Worcester; Cyril Rodgers, Paxton, all of Mass.

[73] Assignee: University of Massachusetts, Worcester, Mass.

[21] Appl. No.: 900,407

[22] Filed: Aug. 26, 1986

Related U.S. Application Data

[63] Continuation-in-part of Ser. No. 828,766, Feb. 11, 1986, abandoned.

[51] Int. Cl.⁴ .............................................. G01N 21/64
[52] U.S. Cl. .................................... 356/417; 350/315; 350/318; 250/461.1; 356/418
[58] Field of Search ................ 356/301, 317, 318, 416, 356/417, 418, 419; 350/523, 526, 527, 528, 315, 318, 317; 250/458.1, 459.1, 461.1, 461.2

[56] References Cited

U.S. PATENT DOCUMENTS

| | | | |
|---|---|---|---|
| 3,913,128 | 10/1975 | Van den Bosch | 358/42 |
| 3,918,793 | 11/1975 | Kraft | 350/527 |
| 4,125,828 | 11/1978 | Resnick et al. | 250/461.2 |
| 4,320,970 | 3/1982 | Dowben et al. | 356/317 |
| 4,443,108 | 4/1984 | Webster | 350/315 |
| 4,573,195 | 2/1986 | de France | 382/6 |
| 4,586,819 | 5/1986 | Tochigi et al. | 356/301 |

FOREIGN PATENT DOCUMENTS

| | | |
|---|---|---|
| 0106721 | 4/1984 | European Pat. Off. . |
| 0164680 | 12/1985 | European Pat. Off. . |
| 1019841 | 11/1957 | Fed. Rep. of Germany ...... 350/526 |
| 2316386 | 10/1974 | Fed. Rep. of Germany ...... 350/526 |
| 2522150 | 8/1983 | France . |
| 2532756 | 3/1984 | France ............................... 250/458.1 |
| 0010035 | 4/1968 | Japan .................................. 350/526 |

OTHER PUBLICATIONS

Chance et al., *The Review of Scientific Instruments*, vol. 42, No. 7, Jul. 1971, pp. 951–957.
Zeidler, *Laboratory Equipment Digest*, vol. 12, No. 7, Jul. 1974, pp. 48, 50–54 56, 57.

*Primary Examiner*—F. L. Evans
*Attorney, Agent, or Firm*—Hamilton, Brook, Smith & Reynolds

[57] ABSTRACT

An accessory is provided to convert a conventional microscope to a microspectrofluorimeter. The accessory includes a filter disc having bandpass filters separated by opaque segments. The filter disc is rapidly and continuously rotated to move the filter sequentially into the optical path between a wideband light source and a microscope sample. Photon counting of radiation from the sample is synchronized to the position of the filters during rotation by means of synchronization marks on the filter disc. The same accessory may be positioned between the sample and a detector to detect emitted light of different frequencies.

48 Claims, 8 Drawing Sheets

MICROSPECTROFLUORIMETER

RELATED APPLICATION

This is a continuation-in-part of U.S. application Ser. No. 828,766, filed Feb. 11, 1986, now abandoned.

BACKGROUND

In scientific research, a material can often be characterized by the response of a fluorescent probe to radiation. In some procedures, a sample is illuminated alternately with light of different wavelengths and the fluorescence of the sample with the different illuminating wavelengths is noted. For example, the calcium ion is believed to control a variety of cellular processes with a high degree of spatial and temporal precision. Calcium has been measured in single living cells with high spatial resolution utilizing a miroscope and a highly fluorescent calcium sensitive dye Fura-2. A sample to which the dye has been added is illuminated alternately with light of 340 and 380 nanometers. The free fluorescent dye fluoresces at about 500 nanometers maximally in response to the 380 nanometer excitation; whereas, the dye associated with the calcium ion fluoresces at about 500 nanometers maximally in response to the 340 nanometer excitation. The concentration of calcium can then be calculated from the formula:

$$[Ca^{++}]_i = K_d[(R-R_{min})/(R_{max}-R)]\beta$$

Where $K_d$ is the effective dissociation constant for the Fura-2-Calcium reaction, R is the ratio of fluorescent intensity at 500 nm with the 340 and 380 nm excitation, $R_{min}$ is the limiting value of R at a calcium concentration of zero, $R_{max}$ is R with fully saturated calcium and $\beta$ is an optical constant for the system which is a measure of the relative quantum yield at 380 nm of the calcium free and calcium saturated dye.

The use of a photomultiplier tube coupled to a microscope to detect the fluorescent light from a microscopic portion of a sample has provided excellent spatial and good temporal resolution for spectrofluorimeters. The microscope must be further modified to provide the alternate light sources. One form of dual frequency light source separates the light into monochromatic beams using interferance gratings and then alternately directs the monochromatic beams to the sample using a rotating mirror. The interference gratings are optically inefficient and the inefficiency is exacerbated by low duty cycles of these systems. Such systems have not provided the high switching speed required for temporal resolution in the order of typical biological or chemical reactions or for avoiding problems due to movement artifacts and the like. Further, the light sources have been difficult to align and maintain and have been very expensive.

SUMMARY OF THE INVENTION

A microscope is adapted as a microspectrofluorimeter. A filter assembly is positioned in an optical path which includes a source of illumination, a sample on the microscope and a detector. The filter assembly includes a plurality of bandpass filters having different pass bands which are circumferentially spaced about a filter axis offset from the optical path. The filters are driven about the filter axis to sequentially move the plurality of filter elements into the optical path and thus change the wavelengths of light passing through the filter assembly. A detector such as a photomultiplier tube with photon counter detects light from a microscopic portion of the sample. Light detection is synchronized with the position of the rotating filters. The filter assembly may be positioned between the source of illumination and the sample in order to sequentially change the wavelengths of the illuminating light. Alternatively, it may be positioned between the sample and the detector to detect different frequencies emitted from the sample.

In a preferred system, the filters are driven by a variable speed continuous drive motor. Reference marks associated with the filter elements are detected to provide indications of the position and the rate of rotation of the filter. A filter disc may include fan shaped filter regions, for passing light of different passbands, separated by opaque regions. The opaque regions are only sufficiently wide to just block the light path in order to provide maximum duty cycle. The photon counting relative to each filter is begun and ended as the opaque regions pass the light path. The light detected with each pass of each filter is normalized to the speed of the filters and to the intensity of the wideband light source.

A conventional microscope with photomultiplier tube can be quickly converted to a microspectrofluorimeter by means of an accessory which connects quickly between a conventional light source and the microscope or between the microscope and the light detector. The accessory includes an optical conduit between a light inlet and a light outlet. An inlet connector at the inlet end of the optical conduit mates with the conventional microscope light source or the microscope. An outlet connector at the outlet end of the optical conduit mate with the microscope or the detector.

A filter assembly is eccentrically mounted relative to the optical conduit. It includes a filter housing and a filter disc within the housing. The filter disc has a plurality of filters circumferentially spaced about a filter axis offset from the optical conduit. The accessory includes a drive motor for rotating the filters about the filter axis. To make the accessory adapted to a wide range of microscopes, the inlet and outlet connectors are identical to the pinned bayonet connectors typically found between light sources and microscopes.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 11 (A-D) are a set of timing charts for the microspectrofluorimeter;

DESCRIPTION OF A PREFERRED EMBODIMENT

Figure 1:
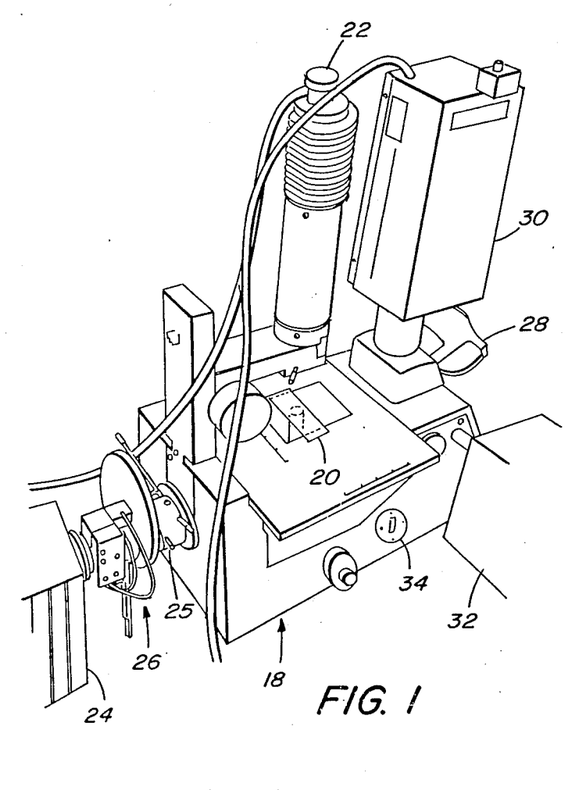
FIG. 1 is a perspective view of a microspectrofluorimeter embodying the present invention.

A conventional microscope 18 modified in accordance with the present invention is illustrated in FIG. 1. A sample slide is shown at 20. The sample may be illuminated from above by a light source 22. Alternatively, a sample may be illuminated from a conventional xenon arc lamp 24 which would typically be connected directly to the microscope at 25. In accordance with the present invention, however, a filter assembly 26 is positioned in the optical path between the light source 24 and the sample 20.

Using either light source, the specimen can be viewed through a binocular viewer 28, and a video output can be provided by a television camera 30. To provide a quantitative indication of the fluorescence from a sample, a photomultiplier tube 32 is coupled to receive most of the light from the sample. In a conventional microscope, a cross-hair assembly extends into the microscope housing to an image plane of the specimen from a closure 34. For the presen invention that cross-hair is replaced by a variable field stop aperture which defines the portion of the sample viewed by the photomultiplier tube.

Figure 2:
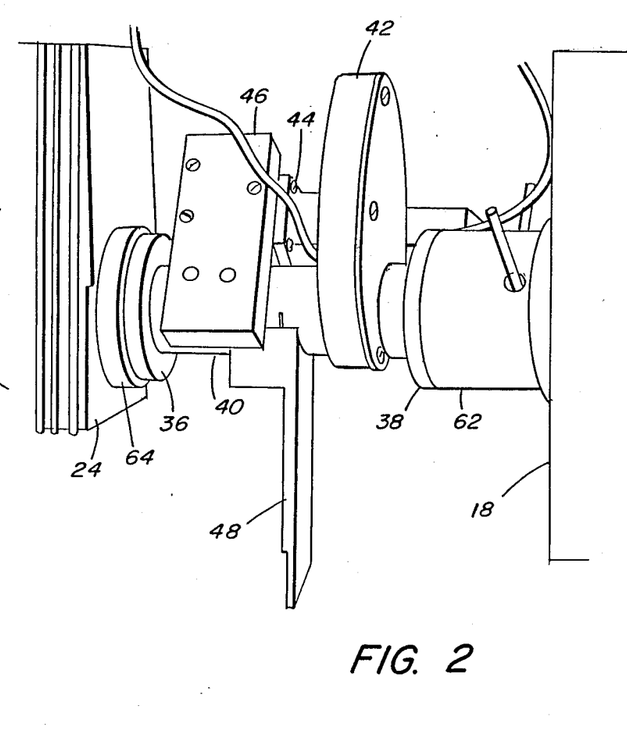
FIG. 2 is an enlarged view of the filter accessory in the system of FIG. 1.

An enlarged view of the filter accessory is shown in FIG. 2. It includes the female portion 36 of a connector for coupling the accessory to the xenon arc lamp 24. The accessory also includes a male portion 38 of a connector for connecting it to the microscope 18. A beam of light from the light source 24 is transmitted through an optical conduit 40 between the connectors. A filter housing 42 is eccentrically mounted relative to the optical conduit and houses a rotating filter disc to be described. The filter disc is rotated by a motor 44 which is mounted to the optical conduit by means of a block 46. A guide 48 is provided for a manual shutter for blocking the light source from the filter assembly.

Figure 3:
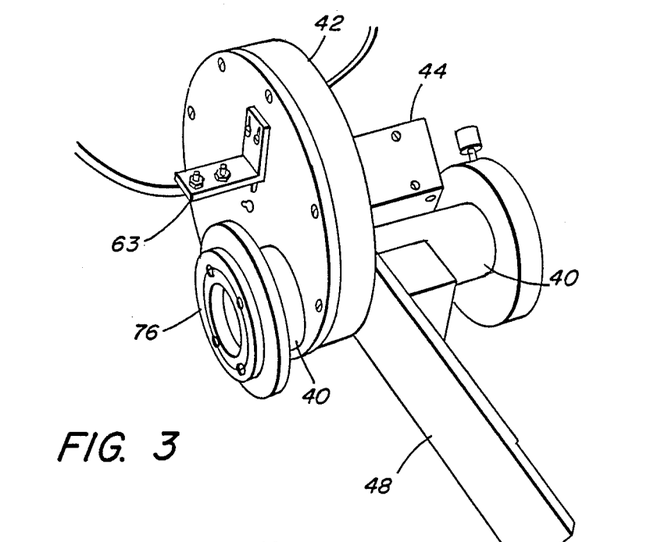
FIG. 3 is a perspective view of the filter accessory removed from the system of FIG. 1 and shown from the rear of FIG. 2.
Figure 4:
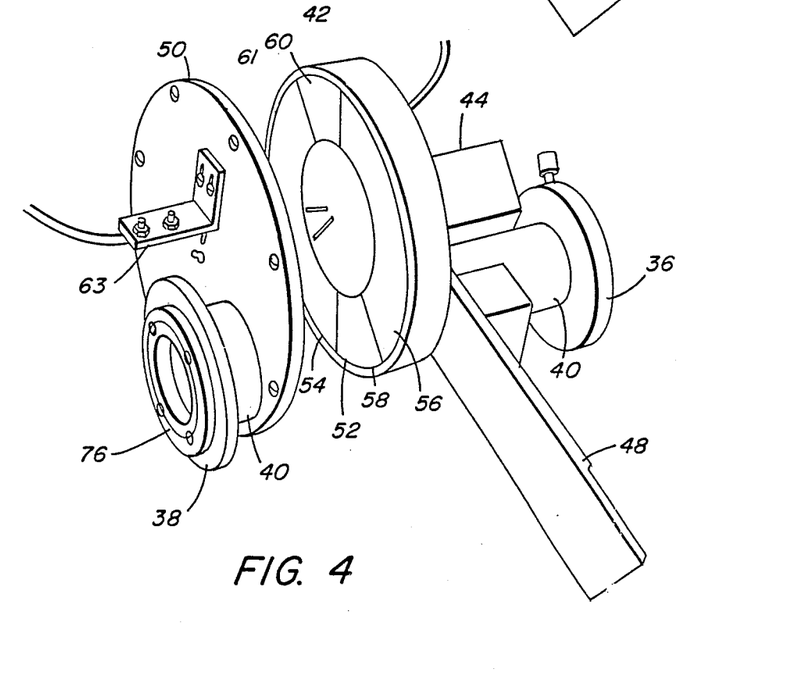
FIG. 4 is a perspective view of the filter accessory of FIG. 3 with the filter housing endcap removed.

The filter accessory removed from the microscope is illustrated in FIGS. 3 and 4. In these figures the accessory is viewed from the rear of FIG. 2. In FIG. 4 the end plate 50 of the filter housing is shown removed. A rigid filter disc 52 is mounted within the housing for rotation about a center axis. The filter disc includes two fanshaped filter regions 54 and 56 separated by opaque regions 58 and 60 in a unitary construction. In a system for determining the calcium ion concentration of the sample using Fura-2 dye, one filter has a pass band centered at 340 nanometers and the other has a pass band centered at 380 nanometers. The specific filters used have a 10 nanometer full bandwidth at half the maximum transmission. As the filter disc is rotated by the motor 44, the two filters are sequentially moved into the optical path through the conduit 40. As will be discussed further below, the opaque regions 58 and 60 are just wide enough to block the light beam in the optical conduit as each is centered at the conduit.

A pair of reflective marks 61 are positioned on the filter assembly and those marks are sensed with each revolution of the filter disc by a light emitting diode and photodetector assembly 63 mounted to the end plate 50 of the housing. The signals from the photo detector synchronize photon counting with rotation of the filter as will be descibed below.

Figure 5:
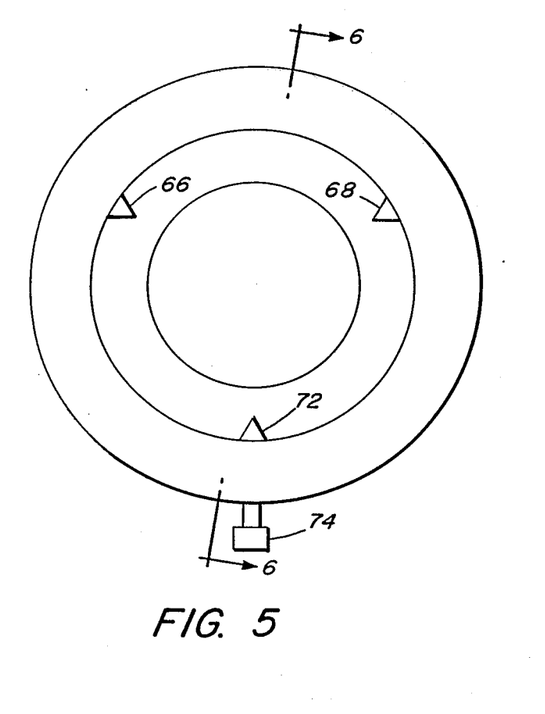
FIG. 5 is an end view of an element of a bayonet optical connector typically mounted to a microscope.
Figure 6:
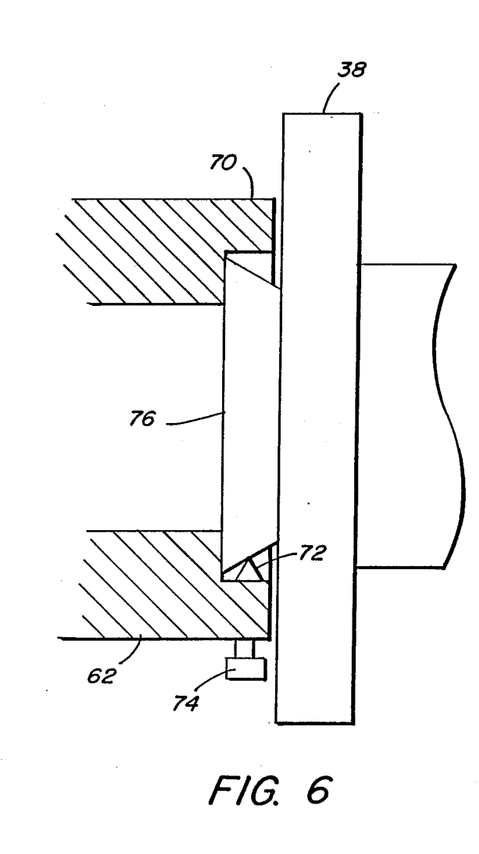
FIG. 6 is a side view, partially in section, of the bayonet optical connector connecting the accessory to the microscope.

In order that the filter accessory can be readily mounted between a conventional microscope and its conventional light source, bayonet optical connectors 36 and 38 as illustrated in FIGS. 5 and 6 are provided. FIGS. 5 and 6 actually show the female portion 62 of the connector typically found on a microscope and the male portion 38 on the accessory. The connector 64 on the xenon arc lamp would be substantially the same as the connector 38, and the conector 36 of the accessory would be functionally the same as connector 62 on the microscope housing.

As shown in FIG. 5, the female portion of the connector includes two fixed pins 66 and 68 which extend radially inward from the rim 70 of the connector socket. A third pin 72 is spring biased so that it can be pulled outward by a pinhead 74. With the pin 72 thus pulled away from the socket, the frustoconical male portion of the connector on the accessory 76 can be slipped behind the pins 66 and 68. When the pin 72 is then released, the pin presses against the conical surface to bring the male portion tightly into the socket. The pin can then be locked into place by manipulating the head 74.

Figure 7:
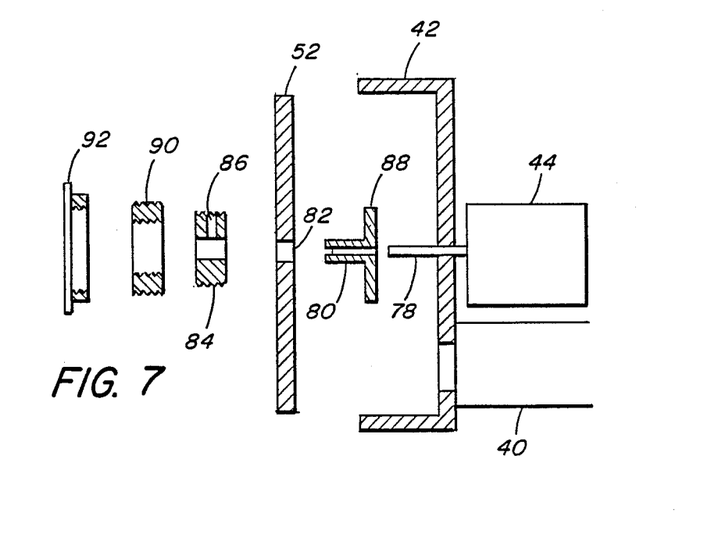
FIG. 7 is an exploded sectional view of the filter assembly.
Figures 8, 9:
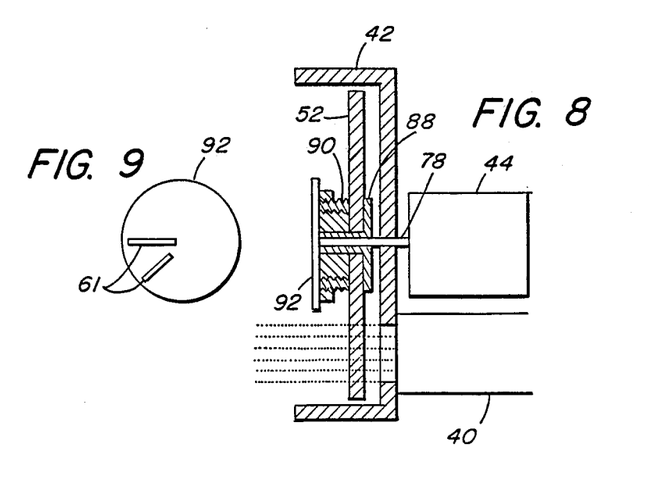
FIG. 8 is a sectional view of the filter assembly.
FIG. 9 is a view of the synchronizing marks on the filter assembly.

The filter assembly is shown in greater detail in FIGS. 7 and 8. A drive shaft 78 extends into the housing of 42 from the drive motor 44. A filter disc carrier 80 is positioned over the drive shaft 70. A clearance of about one mil is provided between the outer diameter of the carrier 80 and the inner diameter of a hole 82 in the filter disc 52 so that the filter can be slid onto the hub of the carrier 80. The hub of the carrier 80 protrudes through the filter disc and a brass retainer 84 is slid over the hub. The retainer 84 is fixed to the carrier 80 by a set screw 86. The set screw also clamps the carrier 80, which is split along its length, onto the drive shaft 78.

The filter disc 52 is pressed snuggly against the flange 88 of the carrier 80 by means of an internally and externally threaded brass sleeve 90 which is threaded onto the retainer 86. The sleeve 90 is also fixed by a set screw. Each of the retainer 84 and sleeve 90 has a pair of holes in the front face thereof for tightening by a two pin wrench. Finally, an end plate 92 is positioned on the assembly and retained by a set screw. The end plate 92 is blackened as shown in FIG. 9 and carries the reflective synchronizing marks 61.

Figure 10:
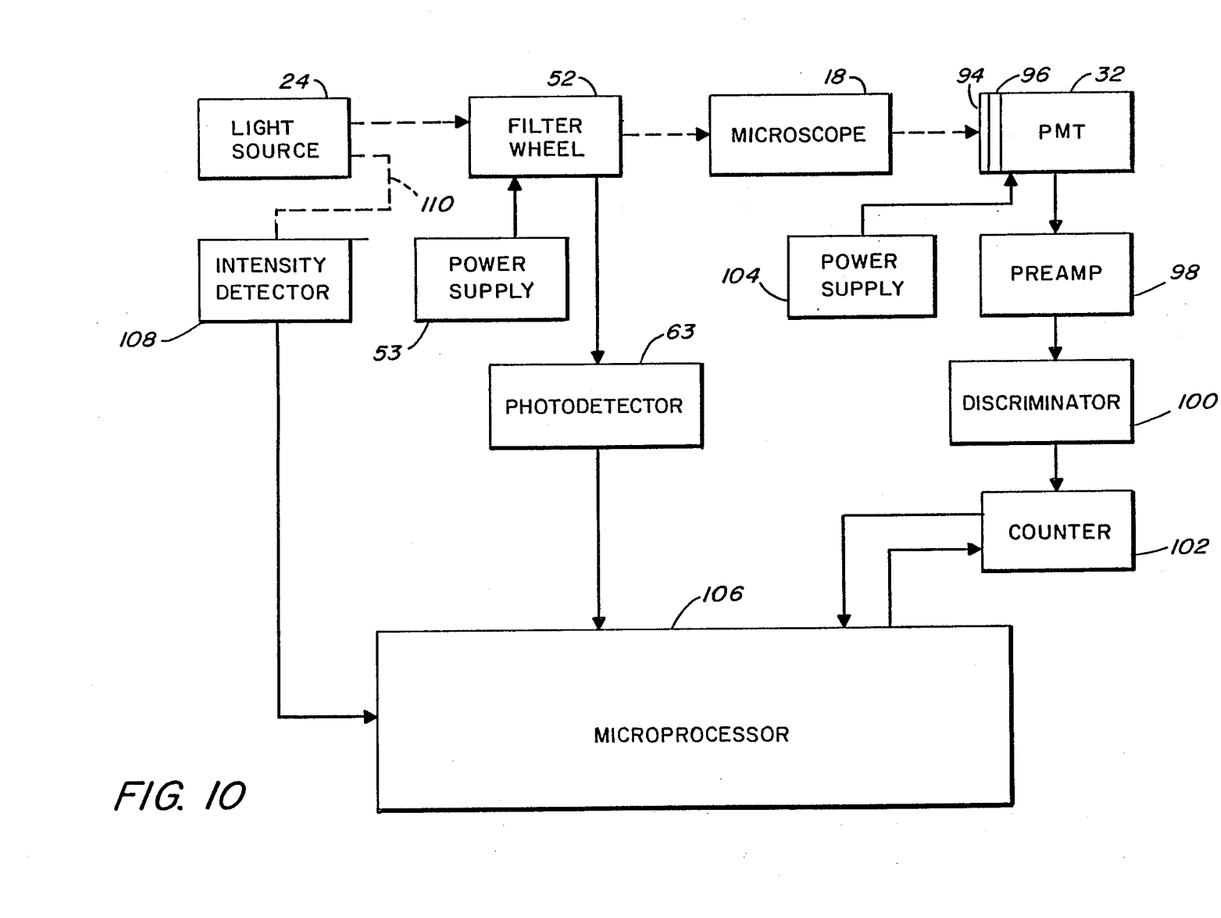
FIG. 10 is an optical and electrical block diagram of the microspectrofluorimeter.

FIG. 10 is a block diagram of the overall system by which microspectrofluorimeter readings are obtained. Light from the light source 24 is directed through the rotating filter disc 52 to illuminate a sample on the microscope 18. Light emitted by the specimen in the microscope 18 is directed to the photomultiplier tube 32. The photomultiplier tube includes a bandpass filter 94 which has a center frequency at 500 nanometers when measuring calcium concentration with Fura-2. The filter passes the light of interest but blocks any light of the excitation wavelengths which may have been reflected from the sample. A shutter 96 is also positioned on the photomultiplier tube.

The output from the photomultiplier tube is amplified by a preamplifier 98 and filtered by a discriminator 100 to eliminate pulses due to noise. The filtered signals are then applied to a photon counter 102. The photomultiplier tube power supply 104, the amplifier 98, the discriminator 100 and the counter 102 are conventional PMT devices such as those provided by Ortec Corporation. The counter 102 has dual channels and it is switched to alternately count photons as the sample is alternately illuminated by the 340 nm and 380 nm light. The counter 102 is switched from one channel to the other by a microprocessor 106, and as photons are counted in one channel the count previously obtained in the other channel is read by the microprocessor and stored. The microprocessor then computes the calcium concentration based on the photon counts during exposure of the sample through each of the 340 nm and 380 nm filters normalized for disc speed. In addition, the microprocessor normalizes for variations in the intensity of the light source 24 by means of a detector 108 which senses the intensity of the light source through a fiber optic bundle 110.

Figure 11A:
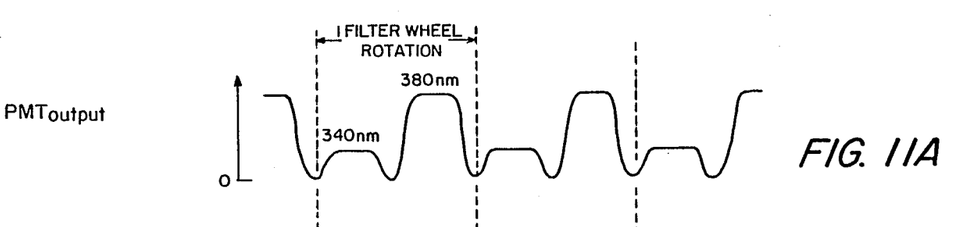
Figure 11B:
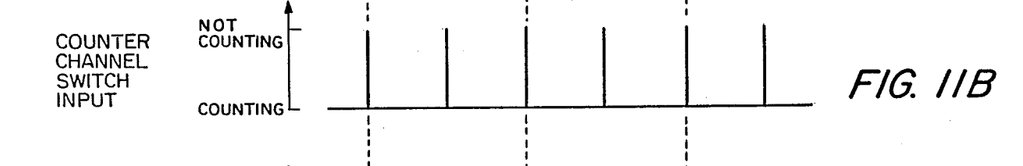
Figure 11C:
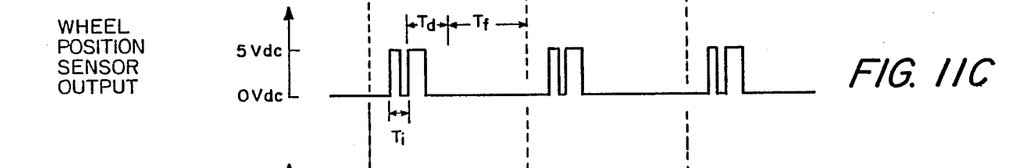
Figure 11D:
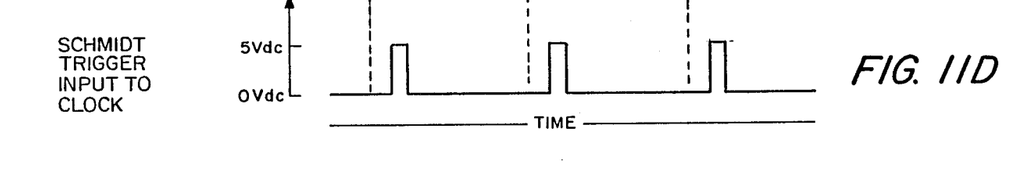

The microprocessor controls switching of the counter 102 between channels based on timing derived from the reflective marks 61 detected by the photondetector 63. The timing of the switching of the counter 102 between the two channels is illustrated in FIG. 11. As already noted, the opaque regions 58 and 60 of the filter disc are just wide enough to completely block the light beam through the conduit 40 when the opaque regions are centered with respect to the conduit. When an opaque region is centered, the photomultiplier tube detects a minimum intensity of fluorescent light. By switching the counter 102 when the opaque regions are centered, each counter channel can count at or near a 50% duty cycle with a plateau of maximum intensity through a substantial portion of each cycle. Thus, near 100% of the photons received by the photomultiplier tube are counted for maximum efficiency. To this end, the pulses for switching the counter between the two channels are, as illustrated in FIG. 11B, centered at the minimum of the PMT output.

Synchronization of the switching with the rotation of the filter disc results from sensing the two reflective marks 61 to obtain the pulses illustrated in FIG. 11C. With the rise of the first pulse, a timing interval is initiated as illustrated in FIG. 11D. With the rising edge of the next pulse as the second mark is sensed, that timing interval is terminated. During the timing interval illustrated by the pulse FIG. 11D, the output of a megahertz clock is counted. The speed of the filter disc is identified by the number of pulses counted, that is the time $T_i$, between sensing of the two marks. Because the location of the synchronizing marks relative to the opaque regions of the filter is known, the time $T_d$ at which the counter channel must next be switched and then the subsequent time $T_f$ at which the counter must again be switched can be readily identified. Because the speed of rotation is determined with each cycle, the system responds immediately to any fluctuations in the speed of rotation of the filter disc. On the other hand, by varying the speed of rotation the temporal resolution of the system can be controlled with the microprocessor 106 responding automatically in each cycle to maintain synchronization of the counter switching with the filter rotation.

Because the microprocessor responds to the filter rotation in controlling switching of the photon count relative to speed of rotation, the photon counting by the combined counter channels is always near one hundred percent. As a result, the system always operates at maximum light collecting efficiency; all light received by the PMT is counted.

A particular application of the present system is in the measurement of fluorescence of ion or molecular sensitive fluorescent probes at two excitation wavelengths to calculate ion or molecule concentrations. For example, calcium ions react with Fura-2 in a reversable reaction of the form $$FX \underset{K_d}{\rightleftharpoons} X + F$$

Where X represents the calcium ion and F the Fura-2 fluorescent dye. The constant of the reaction $K_d$ is defined by $$K_d = \frac{[F][X]}{[FX]}$$

That is, $K_d$ is equal to the product of the concentrations of the free calcium ion and free Fura-2 relative to the concentration of the bonded calcium and Fura-2. The free Fura-2 has its primary fluorescence in response to an excitation wave length of 380 nm. The bonded Fura-2, on the other hand, fluoresces principly in response to an excitation wave length of 340 nm. Both the bonded and unbonded Fura-2 fluoresce at wavelengths centered about 500 nm. Thus, by exciting a sample at separate times with the two excitation frequencies the relative concentrations of the free Fura-2 and the combined Fura-2 can be determined in order to calculate the concentration of calcium ion. The concentration of the calcium ion can be calculated from the following:

$$[X] = K_d (R - R_{min})/(R_{max} - R)\beta$$

where $$R = \frac{I_{340}^{spec} - I_{340}^{blank}}{I_{380}^{spec} - I_{380}^{blank}}$$

I is the sensed fluorescence normalized by the microprocessor to both speed of filter rotation and light source intensity. The subscripts represent the excitation wave lengths. The intensity differences are between that of the test specimen and that of a blank specimen such as a sample of saline solution. $R_{min}$ and $R_{max}$ are respectively the R measured from a sample with only the Fura-2 and no calcium ions and the R measured from totally saturated Fura-2 by providing a sufficiently large amount of calcium ions. $\beta$ is the ratio of fluorescence with only Fura-2 and with saturated Fura-2 each excited at 380 nm.

Thus, in an experimental procedure, a specimen of saline solution is positioned on the sample holder of the microscope and is illuminated through the rotating filter disc to obtain the blank intensity measurements at the respective excitation wavelengths. Then, samples of Fura-2 without calcium ions and Fura-2 saturated with calcium ions are separately positioned on the sample holder and separate measurements are made as each is excited through the rotating filter disc. Finally, a specimen of interest is positioned on the sample holder and is excited through the rotating filter wheel to complete the measurements. All of the data is stored by the microprocessor and is used to compute the calcium ion concentrations.

In many studies it is important to follow the dynamic changes in calcium ion concentration over short time periods. For example, while the calcium concentration in a muscle cell is being monitored, the cell may be electrically or chemically stimulated to contract, and the change in calcium ion concentration during the contraction can be measured. Because the process occurs in the order of milliseconds, it is important that the measurements at both excitation wave lengths be made in the order of milliseconds. To that end, the filter disc is rotated at a rate of up to 12,000 revolutions per minute. With the microscope, the rerevolutions action may be monitored with such rapid response in regions of a sample as small as 0.0625 square microns.

Figure 12:
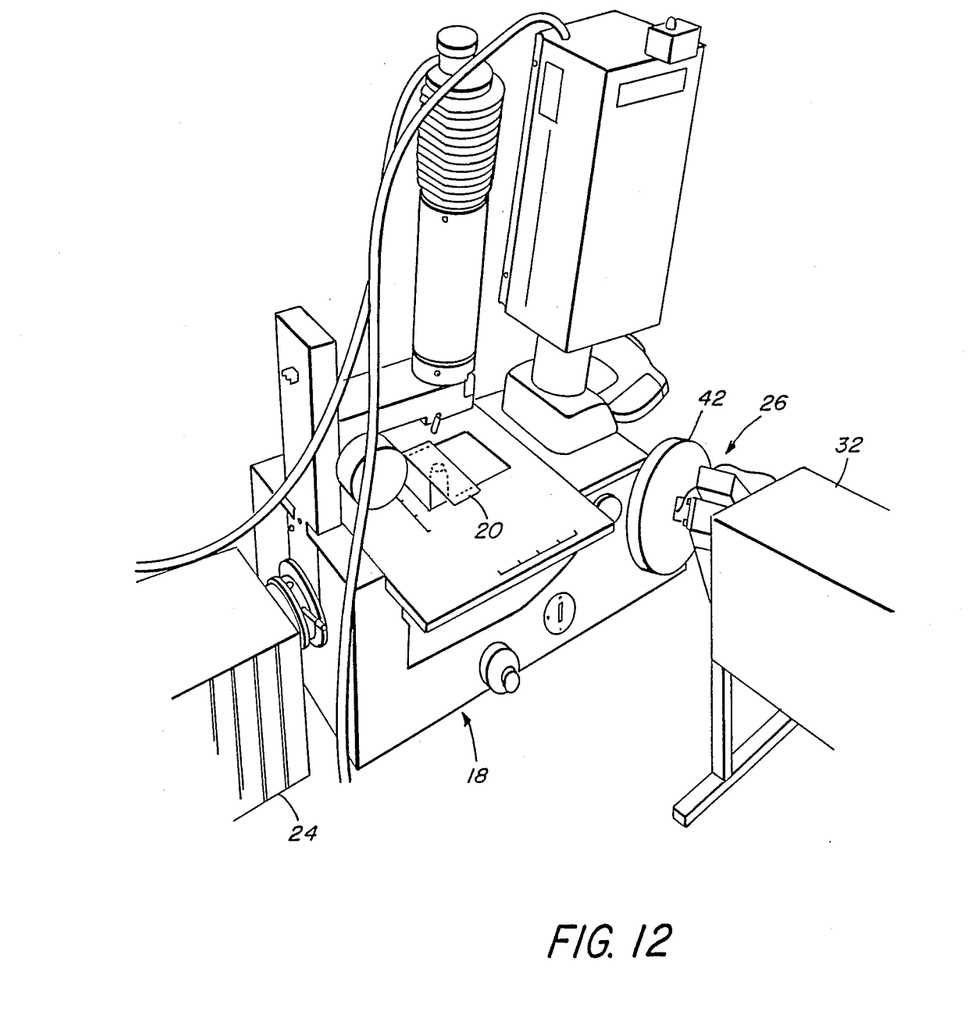
FIG. 12 is a perspective view of the filter assembly mounted in the optical path between the sample and the detector.
Figure 13:
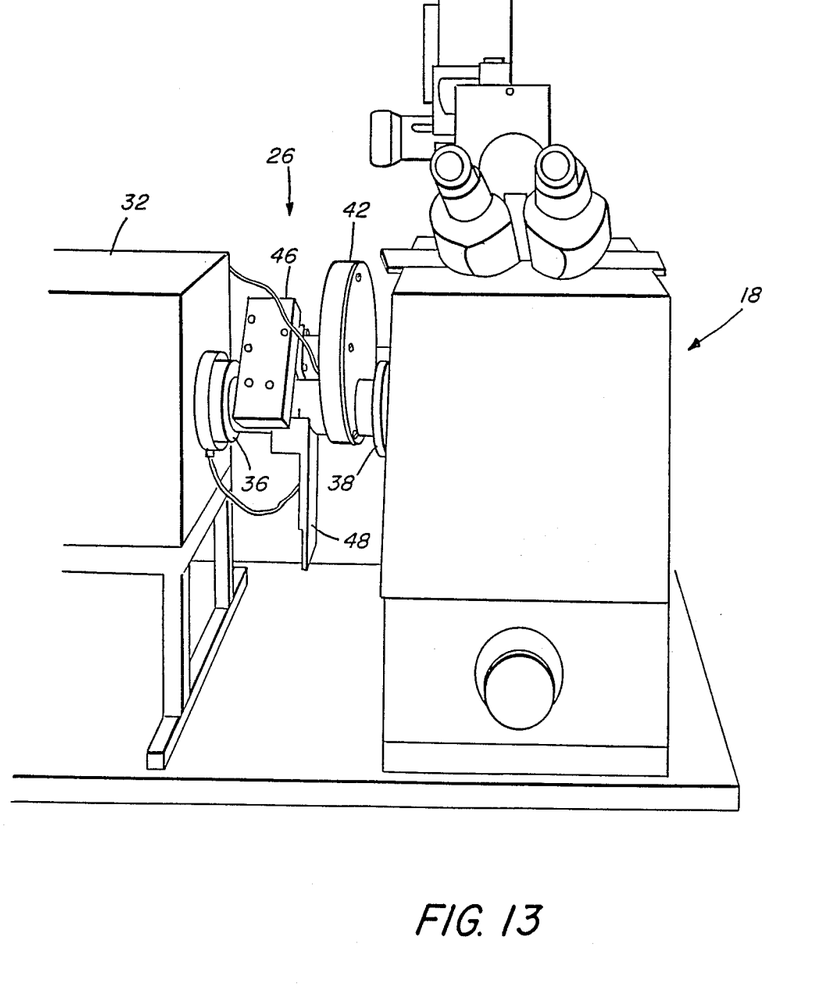
FIG. 13 is a rear view of the filter assembly in the system of FIG. 12.

FIGS. 12 and 13 illustrate an alternative position of the filter accessory 26. The accessory is coupled between the microscope and the detector 32 using the optical connectors 36 and 38 as before. The light source 24 is coupled directly to the microscope. This arrangement may be used to detect different emission wavelengths from molecules with a given excitation wavelength. An example of the systems' use would be in the detection of Indo-1 which also binds to calcium.

The system of FIG. 10 would be unchanged but for the position of the filter wheel 52. Detection through the photon counting photomultiplier tube 32 would be synchronized to the continuously rotating filter as before. The photon counts could be normalized to the speed of the rotating filters and to the intensity of the radiation source.

While the invention has been particularly shown and described with reference to preferred embodiments thereof, it is understood by those skilled in the art that various changes in form and details may be made therein without departing from the spirit and scope of the invention as defined by the appended claims.

We claim:

1. A microscope comprising:
   means for locating a sample;
   a source of radiation for illuminating the sample;
   a detector for detecting radiation from a microscopic portion of the sample;
   a filter assembly in an optical path between the source and the detector, the filter assembly comprising a plurality of bandpass filters having different pass bands circumferentially spaced about a filter axis offset from said optical path and opaque segments between the filters, the width of each opaque segment being such that the opaque segment just blocks a beam of the radiation as the opaque segment is centered on that beam of radiation, and drive means for continuously rotating the filters about the filter axis to sequentially move the plurality of filter elements into said optical path to change the wavelengths of radiation passed through the filter assembly; and
   means for synchronizing the radiation detection with the position of the rotating filters.

2. A microscope as claimed in claim 1 wherein the detector comprises a photomultiplier tube and means for photon counting.

3. A microscope as claimed in claim 1 wherein the drive means comprises a variable speed continuous drive motor.

4. A microscope as claimed in claim 1 wherein the filter assembly further comprises a synchronizing mark fixed relative to the rotating filters and means for detecting the mark as it passes a predetermined position.

5. A microscope as claimed in claim 4 further comprising two synchronizing marks and electronic processor means for computing the speed of rotation of the filters from the time between detection of the two marks.

6. A microscope as claimed in claim 1 wherein the filter assembly comprises a disc having fan shaped filter segments separated by fan shaped opaque segments.

7. A microscope as claimed in claim 6 wherein the filter segments and opaque segments are formed in a unitary filter disc.

8. A microscope as claimed in claim further comprising electronic processor means for controlling cumulative measurement of detected radiation from the sample with illumination of the sample through the respective filters, and the processor terminating the cumulative measurement relative to one filter and beginning the cumulative measurement relative to the other filter as the opaque segments block the radiation.

9. A microscope as claimed in claim 8 wherein the cumulative measurement is by means of a plural channel photon counter and the counter is switched between channels when the opaque segments block the radiation.

10. A microscope as claimed in claim 8 further comprising means for sensing the speed of rotation of the filter assembly, the processor including means for normalizing the cumulative measurements to the speed of the filters.

11. A microscope as claimed in claim 10 further comprising means for monitoring the intensity of the source of radiation and wherein the processor includes means for normalizing the cumulative measurements to the intensity of the radiation.

12. A microscope as claimed in claim 1 wherein the filter assembly is a microscope accessory removably mounted to the microscope.

13. A microscope as claimed in claim 12 wherein the filter assembly accessory is connected to the source of radiation and to a microscope housing which includes the means for locating a sample by means of complementary pinned bayonet connectors.

14. A microscope as claimed in claim 12 wherein the filter assembly accessory is connected to the microscope housing and the detector by means of complimentary pinned bayonet connectors.

15. A microscope as claimed in claim 1 wherein the filter assembly is positioned in the optical path between the source and the sample.

16. A microscope as claimed in claim 1 wherein the filter assembly is positioned in the optical path between the sample and the detector.

17. A microscope as claimed in claim 12 wherein the filter assembly accessory is connected to the source of radiation and a microscope housing which includes the means for locating a sample by means of complementary pinned bayonet connectors.

18. A microscope as claimed in claim 12 wherein the filter assembly accessory is connected to a microscope housing which includes the means for locating a sample and the detector by means of complementary pinned bayonet connectors.

19. A microscope comprising:
 means for locating a sample;
 a source of radiation for illuminating the sample;
 a photomultiplier tube and means for photon counting for detecting radiation from a microscopic portion of the sample;
 a filter assembly in an optical path between the source and the detector, the filter assembly comprising a plurality of bandpass filters having different passbands circumferentially spaced about a filter axis offset from said optical path, the filters being separated by opaque regions of sufficient width for just blocking the radiation;
 a variable speed continuous drive motor, for rotating the filters about the filter axis to sequentially move the plurality of filter elements into said optical path to change the wavelengths of light passed through the filter assembly;
 means for sensing the position and speed of rotation of the rotating filters; and
 electronic processor means for controlling photon counting of detected radiation from the sample, the processor terminating the photon counting relative to one filter and beginning the photon counting relative to the other filter as an opaque segment blocks the source of radiation, the processor including means for normalizing the photon counts relative to the speed of the filters.

20. A microscope accessory comprising:
 an optical conduit between a light inlet and a light outlet;
 an inlet connector at the inlet end of the optical conduit for coupling the conduit into a microscope system;
 an outlet connector at the outlet end of the optical conduit for coupling the conduit into a microscope system;
 a filter assembly eccentrically mounted relative to the optical conduit, the assembly including a filter housing and a filter disc within the filter housing, the filter disc having a plurality of filters circumferentially spaced about a filter axis offset from the optical conduit; and
 drive means for rotating the filters about the filter axis.

21. A microscope accessary as claimed in claim 20 wherein the drive means comprises a variable speed continuous drive motor.

22. A microscope accessory as claimed in claim 20 wherein the filter assembly further comprises a synchronizing mark fixed relative to the rotating filters and means for detecting the mark as it passes a predetermined position.

23. A microscope accessory as claimed in claim 22 further comprising two synchronizing marks and electronic processor means for computing the speed of rotation of the filters from the time between detection of the two marks.

24. A microscope accessory as claimed in claim 20 comprising opaque segments between the filters, the width of each opaque segment being such that it just blocks a beam of light through the optical conduit as the opaque segment is centered on that beam of light.

25. A microscope accessory as claimed in claim 24 wherein the filter assembly comprises a disc having fan shaped filter segments separated by fan shaped opaque segments.

26. A microscope accessory as claimed in claim 20 wherein the filters and opaque segments between the filters ae formed in a unitery filter disc.

27. A microscope accessory as claimed in claim 20 wherein the inlet connector and outlet connector are complementary pinned bayonet connector elements.

28. A filter accessory comprising:
 an optical conduit between a light inlet and a light outlet;
 an inlet connector at the inlet end of the optical conduit for coupling the conduit into an optical system;
 an outlet connector at the outlet end of the optical conduit for coupling the conduit into an optical system;
 a filter assembly eccentrically mounted relative to the optical conduit, the assembly including a filter housing and a filter disc within the filter housing, the filter disc having a plurality of filters circumferentually spaced about a filter axis offset from the optical conduit, the filters being separated by opaque segments each of which just blocks a beam of light through the optical conduit as the opaque segment is centered on that beam of light;
 a variable speed continuous drive motor for rotating the filters about the filter axis; and
 means for detecting a synchronizing mark fixed relative to the rotating filters as the mark passes a predetermined position.

29. A method of measuring the radiation from a sample in response to excitation by radiation of distinct wavelengths comprising:
 positioning a filter assembly between a source of wideband radiation and the sample, the filter assembly comprising a plurality of bandpass filters having different pass bands circumferentially spaced about a filter axis;
 continuously rotating the filters about the filter axis to sequentially move the plurality of filters into the optical path between the source and the sample; and
 counting photons emitted from the samples by beginning and ending photon counting in synchronization with the position of the filters to sequentially count photons emitted as the sample is excited by light through the respective filters.

30. A method as claimed in claim 29 wherein the filters are separated by opaque segments which block the source of wideband radiation and photon counting is switched between channels associated with the respective filters as the opaque regions block the source of wideband radiation such that the duration of photon counting is dependent on the speed of rotation of the filters.

31. A method as claimed in claim 30 further comprising normalizing the photon counts to the speed of the rotating filters.

32. A method as claimed in claim 31 further comprising normalizing the photon counts to the intensity of the wideband radiation.

33. A method as claimed in claim 30 wherein each opaque segment just blocks a beam of the radiation as the opaque segment is centered on that beam of radiation.

34. A method of measuring the radiation of distinct wavelengths from a sample comprising:
 positioning a filter assembly between the sample and a photon counting detector, the filter assembly comprising a plurality of band pass filters having different pass bands circumferentially spaced about a filter axis;

continuously rotating the filters about the filter axis to sequentially move the plurality of filters into the optical path between the sample and the detector; and counting photons emitted from the sample by beginning and ending photon counting in synchronization with the position of the filters to sequentially count photons emitted by the sample through the respective filters.

35. A method as claimed in claim 34 wherein the filters are separated by opaque segments which block the radiation and photon counting is switched between channels associated with the respective filters as the opaque regions block the radiation such that the duration of photon counting is dependent on the speed of rotation of the filters.

36. A method as claimed in claim 35 further comprising normalizing the photon counts to the speed of the rotating filters.

37. A method as claimed in claim 36 further comprising normalizing the photon counts to the intensity of the radiation.

38. A method as claimed in claim 35 wherein each opaque segment just blocks a beam of the radiation as the opaque segment is centered on that beam of radiation.

39. A microscope comprising:
means for locating a sample;
a source of radiation for illuminating the sample;
a detector for detecting radiation from a microscopic portion of the sample;
a filter assembly in an optical path between the source and the detector, the filter assembly comprising a plurality of bandpass filters having different pass bands circumferentially spaced about a filter axis offset from said optical path and drive means for rotating the filters about the filter axis to sequentially move the plurality of filter elements into said optical path to change the wavelengths of radiation passed through the filter assembly, the filter assembly further comprising two synchronizing marks fixed relative to the rotating filters and means for detecting the marks as they pass a predetermined position;
means for synchronizing the radiation detection with the position of the rotating filters; and
electronic processor means for computing the speed of rotation of the filters from the time between detection of the two marks.

40. A microscope comprising:
means for locating a sample;
a source of radiation for illuminating the sample;
a detector for detecting radiation from a microscopic portion of the sample;
a filter assembly in an optical path between the source and the detector, the filter assembly comprising a plurality of bandpass filters having different pass bands circumferentially spaced about a filter axis offset from said optical path and drive means for rotating the filters about the filter axis to sequentially move the plurality of filter elements into said optical path to change the wavelengths of radiation passed through the filter assembly, the filter assembly further comprising opaque segments between the filters of sufficient width for blocking the source of radiation; and
electronic processor means for synchronizing the radiation detection with the position of the rotating filters, the electronic processor means controlling cumulative measurement of detected radiation from the sample with illumination of the sample through the respective filters, and the processor terminating the cumulative measurement relative to one filter and beginning the cumulative measurement relative to the other filter as the opaque segments block the radiation.

41. A microscope as claimed in claim 40 wherein the cumulative measurement is by means of a plural channel photon counter and the counter is switched between channels when the opaque segments block the radiation.

42. A microscope as claimed in claim 40 further comprising means for sensing the speed of rotation of the filter assembly, the processor including means for normalizing the cumulative measurements to the speed of the filters.

43. A microscope as claimed in claim 42 further comprising means for monitoring the intensity of the source of radiation and wherein the processor includes means for normalizing the cumulative measurements to the intensity of the radiation.

44. A microscope comprising:
means for locating a sample;
a source of radiation for illuminating the sample;
a detector for detecting radiation from a microscopic portion of the sample;
a filter assembly in an optical path between the source and the detector, the filter assembly being an accessory removably mounted to the microscope by means of complementary pinned bayonet connectors and comprising a plurality of bandpass filters having different pass bands circumferentially spaced about a filter axis offset from said optical path and drive means for rotating the filters about the filter axis to sequentially move the plurality of filters into said optical path to change the wavelengths of radiation passed through the filter assembly; and
means for synchronizing the radiation detection with the position of the rotating filters.

45. A method of measuring the radiation from a sample in response to excitation by radiation of distinct wavelengths comprising:
positioning a filter assembly between a source of wideband radiation and the sample, the filter assembly comprising a plurality of bandpass filters having different pass bands circumferentially spaced about a filter axis, the filters being separated by opaque segments which block the source of wideband radiation;

continuously rotating the filters about the filter axis to sequentially move the plurality of filters into the optical path between the source and the sample;

counting photons emitted from the samples by beginning and ending photon counting in synchronization with the position of the filters to sequentially count photons emitted as the sample is excited by light through the respective filters, the photon counting being switched between channels associated with the respective filters as the opaque regions block the source of wideband radiation such that the duration of photon counting is dependent on the speed of rotation of the filters; and normalizing the photon counts to the speed of the rotating filters.

46. A method as claimed in claim 45 further comprising normalizing the photon counts to the intensity of the wideband radiation.

47. A method of measuring the radiation of distinct wavelengths from a sample comprising:
positioning a filter assembly between the sample and a photon counting detector, the filter assembly comprising a plurality of bandpass filters having different pass bands circumferentially spaced about a filter axis, the filter being separated by opaque segments which block the radiation;
continously rotating the filters about the filter axis to sequentially move the plurality of filters into the optical path between the sample and the detector; and
counting photons emitted from the sample by beginning and ending photon counting in synchronization with the position of the filters to sequentially count photons emitted by the sample through the respective filters, the photon counting being switched between channels associated with the respective filters as the opaque regions block the radiation such that the duration of photon counting is dependent on the speed of rotation of the filters; and
normalizing the photon counts to the speed of the rotating filters.

48. A method as claim in claim 47 further comprising normalizing the photon counts to the intensity of the radiation.

* * * * *